(12) United States Patent
Bissell

(10) Patent No.: US 8,435,189 B2
(45) Date of Patent: May 7, 2013

(54) COMPOUND CURETTE WITH LAYERED ANTI-PATHOGEN PROTECTION AND LIQUID DELIVERY SYSTEM

(75) Inventor: Pamela Bissell, Ewing, NJ (US)

(73) Assignee: Pamela Bissell, Ewing, NJ (US)

( * ) Notice: Subject to any disclaimer, the term of this patent is extended or adjusted under 35 U.S.C. 154(b) by 0 days.

(21) Appl. No.: 13/225,382

(22) Filed: Sep. 2, 2011

(65) Prior Publication Data

US 2012/0059278 A1 Mar. 8, 2012

Related U.S. Application Data

(60) Provisional application No. 61/379,871, filed on Sep. 3, 2010.

(51) Int. Cl.
*A61B 10/00* (2006.01)

(52) U.S. Cl.
USPC .......................................................... 600/570

(58) Field of Classification Search ................... 600/570, 600/571
See application file for complete search history.

(56) References Cited

U.S. PATENT DOCUMENTS

| | | | |
|---|---|---|---|
| 466,097 A | 12/1891 | Guess | |
| 1,628,275 A | 5/1927 | Robinson | |
| 2,715,899 A | 8/1955 | MacLean | |
| 2,839,049 A * | 6/1958 | MacLean | 600/569 |
| 3,502,082 A | 3/1970 | Chatfield | |
| 4,056,213 A * | 11/1977 | Stern | 222/95 |
| 4,785,796 A | 11/1988 | Mattson | |
| 5,116,346 A | 5/1992 | Yeh | |
| 5,348,023 A | 9/1994 | McLucas | |
| 5,682,665 A | 11/1997 | Svanberg | |
| 5,827,307 A | 10/1998 | Tipton | |
| D423,669 S | 4/2000 | Huttner | |
| 6,113,628 A * | 9/2000 | Borghi | 623/1.16 |
| 6,398,793 B1 | 6/2002 | McGuire | |
| 6,902,339 B2 * | 6/2005 | King | 401/270 |
| 2003/0235541 A1 * | 12/2003 | Maibach et al. | 424/61 |
| 2010/0121219 A1 * | 5/2010 | McCabe et al. | 600/570 |

\* cited by examiner

*Primary Examiner* — Jeffrey G Hoekstra
*Assistant Examiner* — H. Q. Nguyen
(74) *Attorney, Agent, or Firm* — Alexei P. Krasutsky; Center Grove Law, LLC

(57) ABSTRACT

A compound curette for removing tissue samples and delivering liquid and anti-pathogen to the treated area includes a hollow handle that fits a reservoir with a medicated or cosmeceutical solution. A solution is delivered from the reservoir through a channel to a scraping end of the curette by a button activated mechanism. The scraping end of the curette is made of a metal or hard plastic and is covered in anti-pathogen material. The liquid delivery allows placing a medicine or sterilizing solution directly at the locust of the infection. Pathogen inhibition coating provides for a good safeguard to stop or slow bacteria or fungus proliferation. The method of scraping debris and medication delivery is particularly useful for the treatment of onychomycosis, commonly referred to as a fungus infection of the toenail. Main portions of the curette could be detachable, allowing for the easy reservoir replacement and for the use of multiple scraping utensils. Similarly, the device could be manufactured for a single use when all parts are molded together.

12 Claims, 3 Drawing Sheets

COMPOUND CURETTE WITH LAYERED ANTI-PATHOGEN PROTECTION AND LIQUID DELIVERY SYSTEM

CROSS-REFERENCE TO RELATED APPLICATIONS

This application is based on and claims benefit to U.S. provisional applications 61/379,871 filed on Sep. 3, 2010.

BACKGROUND OF THE INVENTION

The present invention relates to surgical instruments, more specifically to surgical cutting instruments also known as curettes. A curette is a surgical instrument used for scraping biological tissue or debris in various medical procedures. Usually, the curette is a small tool with a handle and a tip in a form of a small scoop, loop or gouge. Among other things, curettes are used in a biopsy, cleaning procedures or excisions. Curettes are very useful in performing delicate tasks where the access with larger equipment is impracticable or would pose danger to patient.

Particularly, the present invention could be used in amelioration of onychomycosis, commonly referred to as a fungus infection of the toenail. This disease also sometimes afflicts the fingernails. According to Harvard Medical School editorial board for InteliHealth.com, Onychomycosis is an extremely prevalent condition in the United States and throughout the world, affecting 2% to 18% of all people worldwide and 3% to 5% of people in the United States. It is relatively rare in children, affecting only about 1 out of every 200 people younger than 18. However, the likelihood of getting toenail fungus increases with age. Up to 48% of people have at least one affected toe by the time they reach age 70.

Despite large numbers of affected people, only about 2.5 million Americans see a podiatrist annually for treatment of toenail fungus. Huge portion of population is infected but never seek help. Some people consider toenail fungus just a cosmetic problem and don't bother seeking treatment.

Toenail fungus is generally treated with prescription anti-fungal medications, both systemic, which are administered orally, and topical, which are applied to the affected area directly. These are sometimes used in combination. When either or both are used, they are frequently supplemented by debridement of both the fungi and the keratin debris which forms fungi's main feedstock. This debridement has been reported to significantly enhance the treatment. The usual instrument employed for nail debridement comprises an either open or closed cup, spoon, or scoop-shaped curette.

DISCUSSION OF PRIOR ART

There are multiple designs and styles for curettes for scraping tissue. Unfortunately, most of them have serious disadvantages, especially if applied in toenail treatment. Some of described curettes include loop-shaped blades in the circular, teardrop, oval or other configurations. Those are usually unsuitable to treat the nail fungus. Onychomycosis treatment involves the scraping of the lower side of the nail by inserting the instrument between the nail and the nail bed. The nail is not innervated, so there is no feeling transmitted to the subject. However, the nail bed is highly sensitive to pain and must not be subjected to any scraping or other rough treatment. The very nature of the band loop type of curette makes it impossible to ensure protection to the nail bed.

For the same reason a spoon shaped (ellipsoid) curette with sharpened edges designed to remove debris by rotation is not usable to work under the toenail. Rotation of the instrument with sharp edges will likely injure a delicate nail bed. Similarly to loop-shaped, curettes designed as circular openings in a scalpel blade are unsuitable for nail fungus treatment.

In addition, none of the prior art curettes addressed the issue of pathogen proliferation. Surgical or cosmetic procedure necessitates maximum sterilization of every instrument. While the subject of hardness and crack resistance was addressed in prior art curettes, none had offered any pathogen safeguards. Propagation of bacteria and fungus is undesirable side effect of any surgical or cosmetic procedure. In medical devices, there are several different techniques to halt unwanted transfer and growth of bacteria. For instance, it could be done via anti-pathogen coating or by delivering a cleaning or medicating agent to the area of scrubbing. None of the prior art curettes have a capability to effectively supplement their action by delivering cutting fluids, medications, or anti-pathogen liquids to the area of scrubbing. It has been done by adding a liquid solution either through the use of a separate delivering device, pipette or small brush, or by fluid delivery through a tube external to the curette shaft, and a shaft with a lumen to conduct the fluid. In neither of the prior art methods the liquid delivery is integral with the tool.

Toenail treatment requires one hand of the treatment provider to steady the toe. The other hand should work fast and with precision, to provide comfortable and painless experience for the patient. The delivery of medicine or anti-pathogen to the tip of the toenail scrubbing curette is unfeasible with prior art curettes, unless a second treatment provider is involved. None of the prior art curettes are adapted to stop the bacteria or fungal growth. Usually it is done with a separate device.

Thus, there is a clearly felt need for a new curette which will be designed to work under the nail without injuring the patient, will stop pathogen growth or transfer of bacteria or fungus from the infected to a healthy nail, and has an additional function of delivering a cleaning or medicating solution directly to the curette's tip. At the same time, such device would be desired in many other surgical and cosmetic applications.

The disclosed invention addresses these and some other issues related to the current state of curette surgical technology.

SUMMARY OF THE INVENTION

Accordingly, the primary objective of the present invention is to provide a curette which is shaped and designed to allow scrubbing underneath the affected toenail without injuring the sensitive nail bed, will stop or slow pathogen proliferation, has a liquid delivery system installed in the handle portion of the curette, to deliver medicated or cosmeceutical solution to the tip portion of the curette.

According to the present invention, medicated solution refers to any over-the-counter or prescription liquid medication that could be used for the treatment in conjunction with cleaning or surgical procedure. For instance, medicated solution could be any liquid topical medication used for the treatment of onychomycosis. Cosmeceuticals are cosmetic products with biologically active ingredients purporting to have medical or drug-like benefits. Cosmeceutical solutions could include, but are not limited to sterilizing liquids, creams, lotions, and ointments.

The proposed curette described in present invention includes a hollow handle with the room for a liquid container and a pumping mechanism, and at least one scraping implement, attached to one end of the handle by means of the narrow hollow shaft for delivering the liquid from the container to the scraping tip. The handle is sized to fit a palm of the hand with the cross-section comfortably fitting between a thumb and an index finger. One end of the handle is rounded to provide convenient rest at the base of the hand palm close to the wrist. The handle could be equipped with a single or multiple buttons, located closer to the shaft end to activate the mechanism of liquid delivery.

The reservoir containing liquid is placed in the handle to feed the liquid to a lumen in the shaft between the handle and the curette scoop. This liquid could be a saline solution for lavage, a solution to soften the keratin debris to facilitate its removal, a disinfectant or antifungal solution, or any other appropriate liquid. This liquid would enter the scoop through small orifice, and could be controlled by actuating a pump, or in the case of a pressurized reservoir, by a valve on the handle, or it could flow continuously, depending on the desire of the user. The liquid flow will also loosen and help eject any slug of material that has been removed by scraping.

The reservoir could be made from a soft polymer material selected from but not limited to polyethylene, polypropylene, polyvinylchloride, polyurethane, etc. Softness will allow the easy pressure generation by simple squeeze of a thumb or finger to the button. The reservoir could also be made from a solid and pressure resistant material if the pressure generating mechanism involves the use of a pressurized gas.

The lumen is preferably designed such that the opening closest to the reservoir has a smaller diameter and the end connected to the scraping end has a larger opening. This will reduce the likelihood of clogging, because anything that passes through the small end will likely pass all the way through the lumen and into the bowl.

The liquid reservoir can be implemented in a number of ways, preferably excluding the air in the liquid reservoir so that the instrument can be used in any position. An air-over-liquid arrangement would leak air if the instrument were pointed upward and the valve opened. This can be circumvented by interposing a bladder with an external compression arrangement, or alternatively, the instrument could be designed instead to use a piston compressed by an external spring, or other similar means. Similarly, a pump driven system could utilize either a bladder or the reservoir could have a passive piston following the liquid level as it is depleted. The piston will be driven by atmospheric pressure as the liquid is pumped out of the reservoir, thus creating a negative pressure in the fluid chamber.

The scraping end is preferably round in shape with a scoop in form of a cup. The bottom part of a scoop is round and smooth, designed to prevent injury to a sensitive part of a nail bed. A scraping edge of the scoop is a round sharp edge allowing for effective scraping of affected areas underneath a toenail. A cup shape provides for more efficient liquid containment and delivery to the treated area.

The scraping end is made of or is coated with an anti-pathogen material, providing an extra safeguard from bacterial or fungal proliferation during the treatment. Such protection could be accomplished by plating the base metal, usually stainless steel, with a metallic surface that possesses anti-bacterial, antiviral, and/or antifungal properties. Such metals could be selected from but are not limited to: silver, copper, zinc, cobalt, nickel, selenium, or compound metals such as copper-containing titanium nitride films, titanium-hafnium, titanium, plus chromium, titanium nitride plus hafnium nitride, titanium nitride plus zirconium nitride, titanium nitride plus chromium nitride or titanium dioxide. The titanium nitride combinations are interesting because titanium nitride also confers anti-corrosion and anti-wear properties when deposited on other surfaces, such as stainless steel. The above materials are presented as examples, and not intended to limit the possible metals or combination of metals that could be used.

Similarly, the scraping end could be made from a hard polymer material and coated with an anti-pathogen agent. The use of plastic would make the curette more economical, providing cheaper disposable instrument. One of the alternative embodiments of the present invention represents a curette molded entirely out of plastic.

The scraping end is connected to the handle by a short and hollow tube (lumen), allowing the transport of liquid from the container inside the handle to a scraping implement. The tube on one end is connected to a handle and on the other end to a scraping scoop. The tube is made of a stainless steel or a polymer material. It is feasible to have a top portion of a handle to be removable and solidly attached to a short tube with a scoop. Such part could be reusable and attachable to a handle by means of a screw thread connection.

It is a further object of the present invention to provide a corrosion resistant, anti-pathogen coated curette which delivers an antifungal, anti-bacterial, antiviral liquid to the locus of the infection.

The present invention should not be restricted to the treatment of onychomycosis. It could be used for any other nail ailments as well as for other surgical procedures.

Additional features of the disclosure will become apparent to those skilled in the art upon consideration of the following detailed description of the illustrative embodiment.

BRIEF DESCRIPTION OF THE DRAWINGS

The detailed description particularly refers to the accompanying figures in which.

DETAILED DESCRIPTION OF PREFERRED EMBODIMENTS

Figure 1:
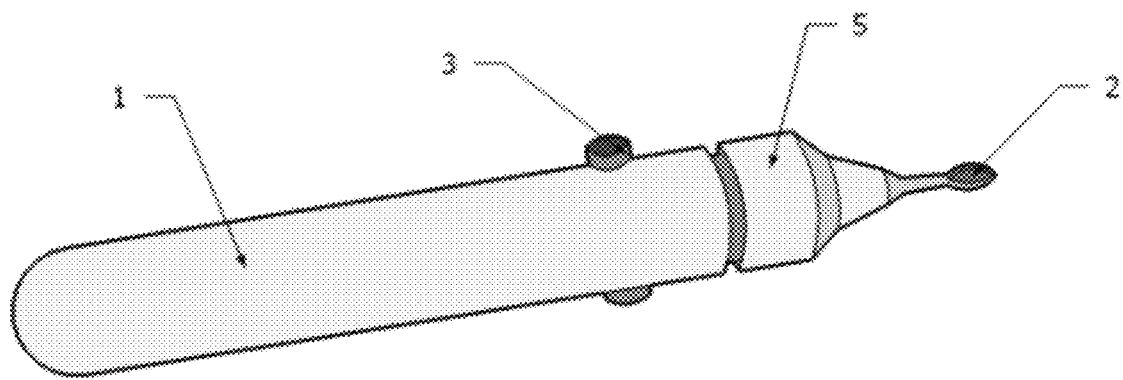
FIG. 1 is a prospective view of a curette with anti-pathogen protection and liquid delivery system according to the present invention.

For the purposes of promoting and understanding the principles of the invention, reference will now be made to one or more illustrative embodiments illustrated in the drawings and specific language will be used to describe the same.

Referring to FIG. 1, a curette with anti-pathogen coating and liquid delivery system includes a handle 1 made out of s polymer plastic or metal and hollow inside. One end of the handle is rounded to fit comfortably at the palm of user's hand. The other end has a detachable scraping implement 2 that is attached to a removable portion of the handle 5. Scraping implement is usually made out of the hard material like stainless steel and coated with the pathogen inhibiting material selected but not limited to the following: silver, copper, zinc, cobalt, nickel, selenium, or compound metals such as copper-containing titanium nitride films, titanium-hafnium, titanium, plus chromium, titanium nitride plus hafnium nitride, titanium nitride plus zirconium nitride, titanium nitride plus chromium nitride or titanium dioxide or the mixture thereof. Scraping implement could be made entirely out of a pathogen inhibiting material. The handle is fitted with at least one button 3 to activate a liquid delivery from a reservoir located in the handle towards a scraping implement.

Figure 2:
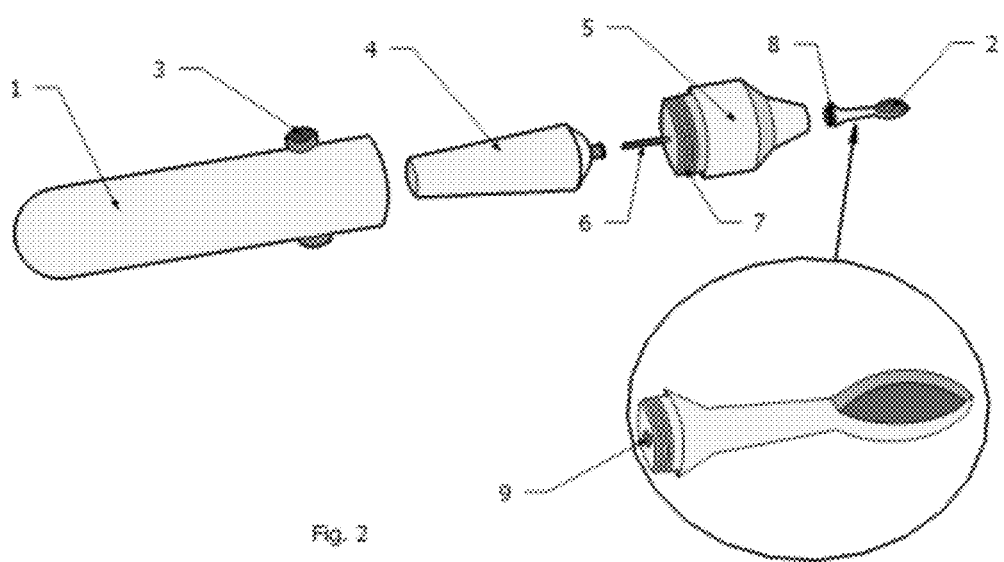
FIG. 2 is an exploded prospective view of a disassembled curette according to the present invention.

As could be seen from FIG. 2, the handle of curette opens up to fit a reservoir 4 filled with a cosmeceutical or medicated solution. The rounded portion 1 could be attached to a detachable part 5 by means of a screw thread 7. The tip with a scraping implement 2 could be reusable and attachable to part 5 by means of screw thread 8. The tip portion of the curette is shown in exploded view to demonstrate a thread and a burrow 9 that allows liquid to travel from reservoir 4 through needle 6 to a scraping scoop 2. The threaded detachable part 5 is fitted with a needle 6 that is meant to penetrate a cup of a reservoir 4. Buttons 3 are designed to apply pressure on the reservoir 4 to create a flow of the medicine towards the scraping implement. For that reason, reservoir 4 should be made out of a soft plastic like material. Reservoir 4 could be reusable or it could be manufactured and filled with a desired solution, and refilled after each use.

Figure 3:
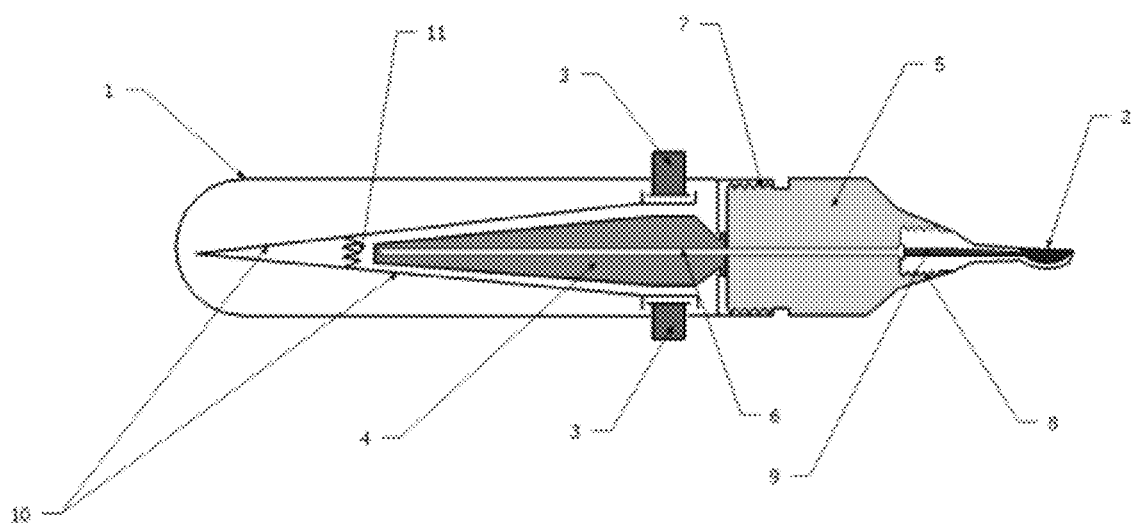
FIG. 3 is a cross sectional view of a curette with a liquid delivery system in accordance with the present invention.

FIG. 3 provides a cross sectional view of the present invention. The scraping implement with a scoop 2 is attached via a screw thread 8 to a detachable portion of the handle 5. Scoop is connected to a main liquid channel by means of a burrow 9. The detachable portion 5 has a hole in the middle, fitted with a long needle 6 that matches the opening of the burrow 9. The length of the needle is designed to almost reach the bottom of the reservoir 6, filled with either liquid medication or a cleaning solution. Part 5 is fitted to the rest of the handle 1 by means of a screw thread 7, to precisely secure the top of the plastic reservoir 4 in place of a narrow opening in the handle. Buttons 3 are set in their location by means of a metal v-shaped clip 10. The clip is kept opened by a spring 11, installed close to the end of the reservoir 4. The spring 11 keeps buttons erected, and returns them in position after every squeeze. Upon application of force to buttons 3, the pressure is generated inside of the reservoir 4, squeezing the liquid through the needle 6 towards the burrow 9, making its way to a scraping scoop 2. The device is designed to conveniently fit the palm of the user's hand, so the buttons could be pressed by the thumb and the index finger, without interrupting a scraping action. Present embodiment represents the most economical design, and should not be considered limiting. Other more complex pumping mechanisms could be used, allowing for a more controlled release of the liquid from a reservoir.

Figure 4:
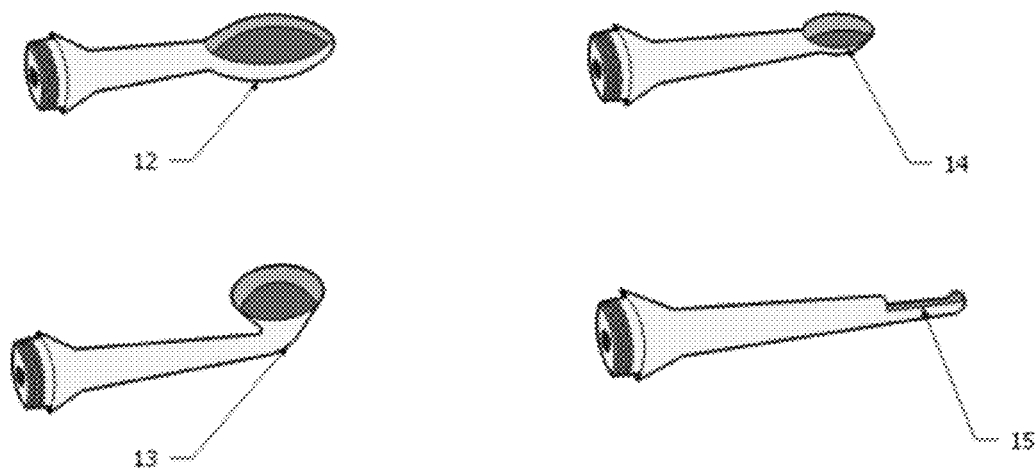
FIG. 4 is an enlarged prospective view of detachable scraping implements in accordance with the present invention.

FIG. 4 demonstrates different designs of the scraping implement. Present invention is not meant to be limited only to a toenail treatment. Nevertheless, all of the designs presented have an opening at the top and a smooth bottom. Scoops 12 and 14 are similar and differ mainly in the size of the opening of the cup. Detachable scraping implement 13 ends with a cone-shaped cup, attached to a shaft at the bottom portion. Such implement could be effective in the treatment of common warts. Duct-like design of the implement 15 allows for a deeper penetration and could be very useful in the nail treatment. All of the scraping implements according to a present invention are made from either a hard metal, like stainless steel or a hard polymer material. The base material could be coated with a material that demonstrated a pathogen inhibition. Such coating, combined with a delivery of the medication to the locus of the infection makes the current invention significantly more efficient than previously described curettes.

Figure 5:
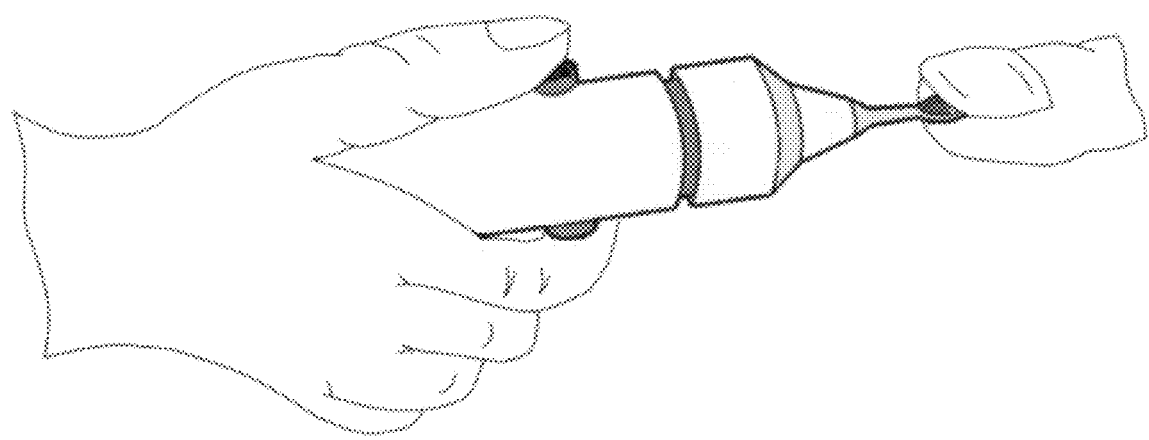
FIG. 5 is a prospective view of a toenail scrubbing application of a curette with liquid delivery system, according to present invention.

The curette with anti-pathogen coating and liquid delivery system is utilized to treat onychomycosis or other nail ailments by removing keratin debris, fungi, and other undesirable materials that may have accumulated in the affected area. The coating helps to stop or slow the dangerous pathogen proliferation. This feature is greatly important in cosmetic and surgical treatment. Usually, the same curette is used to treat all nails of the patient, requiring frequent sterilization while working from toe to toe. The anti-pathogen coating serves as an additional safeguard, denying the spread of the fungus from an affected nail to a healthy one. A convenient liquid delivery system, manipulated by a simple squeeze of a thumb, allows treating the infection in previously unreachable areas. FIG. 5 provides a prospective view of the application of the present invention for the treatment of a toenail ailment.

In the pictured on FIG. 5 intended use, the practitioner holds the solid handle and maneuvers the curette cup attached to a solid handle by solid shaft between the nail and the nail bed of the selected toe or finger. The curette cup is oriented to face upward toward the nail, applying light pressure upward. The curette cup is used to scrape off and scoop away any keratin debris, fungi, and other undesirable materials that may have accumulated in this space. The curette bowl is sometimes rotated in order to facilitate this removal process. As the bowl fills with accumulated debris, it is retracted and emptied. When the procedure is finished, any debris clinging to the curette with layered anti-pathogen protection is mechanically removed by the practitioner or staff, and the curette is sterilized using any of the standard methodologies.

Figure 6:
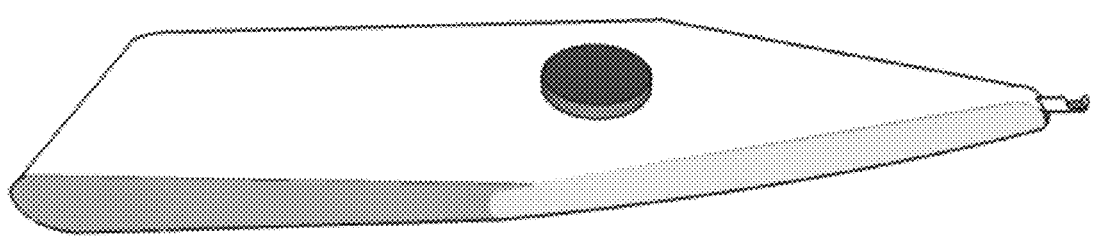
FIG. 6 is a prospective view of an alternative embodiment of a curette according to the present invention molded entirely out of plastic.

As pictured in FIG. 6, the alternative embodiment of the present invention could be molded entirely out of hard plastic. Such device is meant to be disposable and could be manufactured with a reservoir with a desired liquid solution already placed in the plastic mold. There are no detachable parts, and the handle could be simply sealed from the end opposite to a scraping end, after placing a reservoir inside. Similarly to the described detachable curette, the reservoir should be connected to the shaft leading to the scraping implement. The button could be placed anywhere on the handle to provide for the most comfortable use. The scraping end is molded from the same hard plastic and could be coated with an anti-pathogen agent. Some of the hard plastic materials that could be used are: polypropylene, polyacrylonitrile and polycarbonate. It should be understood, that present invention is not limited to the use of those three materials. Any other durable polymer could be used.

Figures provide preferred embodiment of the invention. However, the invention is not limited to the disclosed configuration. The liquid delivery system could be more complex, allowing for the measured delivery of prescription medication.

While the invention has been illustrated and described in detail in the foregoing drawings and description, the same is to be considered as illustrative and not restrictive in character, it being understood that only illustrative embodiments thereof have been shown and described and that all changes and modifications that come within the spirit and scope of the invention as defined in the following claims are desired to be protected.

The invention claimed is:
1. A compound curette for removing tissue samples and delivering liquid and anti-pathogen to the treated area comprising:
   a handle having a first end and a second end, said handle having a hollow chamber inside;

a scraping utensil being attached at said second end, said scraping utensil having an opening with sharp edges for scraping and removing the tissue samples;

said scraping utensil having a burrow connecting said opening with sharp edges to said hollow chamber inside said handle;

a separable reservoir fitting said hollow chamber inside said handle;

said handle fitted with means for applying pressure around said separable reservoir and fitted with means of delivering the liquid and anti-pathogen from said separable reservoir to said scraping utensil via said burrow for treatment.

2. The compound curette for removing tissue samples and delivering liquid and anti-pathogen to the treated area of claim 1, further comprising:

said means for applying pressure around said separable reservoir being a metal plate fitted inside said hollow chamber and folded in a V-shape wherein said separable reservoir fits inside said metal plate;

a spring, fitted inside said metal plate to keep it open;

a button to apply pressure on said metal plate, squeezing said spring and squeezing said separable reservoir;

said means of delivering the liquid and anti-pathogen from said separable reservoir to said scraping utensil via said burrow being a needle attached to said burrow and sized to penetrate said separable reservoir and reach the liquid from said separable reservoir;

wherefore sufficient force may be applied to said button causing the metal plate to compress and squeeze said separable reservoir, sending the liquid from the separable reservoir to said needle and farther through said burrow to said opening with sharp edges of said scraping utensil.

3. The compound curette for removing tissue samples and delivering liquid and anti-pathogen to the treated area of claim 1, wherein said handle and said scraping utensil are made entirely of polymer selected from the group consisting of polypropylene, polyacrylonitrile, polycarbonate, polyvinylchloride and polyurethane.

4. The compound curette for removing tissue samples and delivering liquid and anti-pathogen to the treated area of claim 1, wherein said second end is detachable from said handle, providing an access to said hollow chamber inside said handle.

5. The compound curette for removing tissue samples and delivering liquid and anti-pathogen to the treated area of claim 1, wherein said scraping utensil is detachable from said second end of said handle.

6. The compound curette for removing tissue samples and delivering liquid and anti-pathogen to the treated area of claim 1, wherein said scraping end is coated with metal selected from the group consisting of silver, copper, zinc, cobalt, nickel and selenium.

7. The compound curette for removing tissue samples and delivering liquid and anti-pathogen to the treated area of claim 1, wherein said scraping end is coated with anti-pathogen compound selected from the group consisting of copper-titanium nitride, titanium-hafnium, titanium-chromium, titanium nitride-hafnium nitride, titanium nitride-zirconium nitride, titanium nitride-chromium nitride and titanium dioxide or a mixture thereof.

8. The compound curette for removing tissue samples and delivering liquid and anti-pathogen to the treated area of claim 1, wherein said separable reservoir is filled with a medicated solution.

9. The compound curette for removing tissue samples and delivering liquid and anti-pathogen to the treated area of claim 1, wherein said separable reservoir is filled with a cosmeceutical solution.

10. A method for removing tissue samples with the compound curette for removing tissue samples and delivering liquid and anti-pathogen to the treated area of claim 1, said method comprising the steps of:

(a) providing the compound curette for removing tissue samples and delivering liquid and anti-pathogen to the treated area of claim 1;

(b) scraping tissue with said scraping utensil of said compound curette;

(c) applying pressure to said separable reservoir to cause said liquid to travel to said scraping utensil; and (d) applying said liquid to abraded tissue.

11. A method of claim 10, wherein said method is used for a treatment of toenail ailments.

12. The compound curette for removing tissue samples and delivering liquid and anti-pathogen to the treated area of claim 1, wherein said separable reservoir is made from a soft polymer material selected from the group consisting of polyethylene, polypropylene, polystyrene, polyvinylchloride and polyurethane.

* * * * *